United States Patent
Convert et al.

(10) Patent No.: US 8,262,997 B2
(45) Date of Patent: Sep. 11, 2012

(54) MICRO-VOLUMETRIC BLOOD RADIOACTIVITY COUNTER

(75) Inventors: Laurence Convert, Katevale (CA); Jules Cadorette, Ascot Corner (CA); David Lapointe, Pointe-Claire (CA); Roger Lecomte, Sherbrooke (CA)

(73) Assignee: Société de Commercialisation des Produits de la Recherche Appliquée-Socpra Sciences Sante et Humaines S.E.C., Sherbrooke, Quebec ( * ) Notice: Subject to any disclaimer, the term of this patent is extended or adjusted under 35 U.S.C. 154(b) by 1087 days.

(21) Appl. No.: 11/378,420

(22) Filed: Mar. 17, 2006

(65) Prior Publication Data

US 2006/0279724 A1    Dec. 14, 2006

Related U.S. Application Data

(60) Provisional application No. 60/662,387, filed on Mar. 17, 2005.

(51) Int. Cl.
*G01N 33/00* (2006.01)

(52) U.S. Cl. .. 422/73; 422/71; 250/363.04; 250/363.05; 250/364; 250/370.09; 356/39

(58) Field of Classification Search ............ 422/73, 422/71; 250/363.04, 363.05, 364, 307.09; 356/39

See application file for complete search history.

(56) References Cited

U.S. PATENT DOCUMENTS

| 4,682,035 A | | 7/1987 | Shulman |
| 5,143,850 A | * | 9/1992 | Pentoney et al. ............. 204/452 |
| 6,130,098 A | * | 10/2000 | Handique et al. ............. 436/180 |
| 2005/0127300 A1 | | 6/2005 | Bordynuik |

FOREIGN PATENT DOCUMENTS

WO    WO 9961880 A2 * 12/1999

OTHER PUBLICATIONS

Derenzo, S.E et al, "Initial Characterization of a Position-Sensitive Photodiode/BGO Detector for PET", IEEE, vol. 36, No. 1, Feb. 1989, pp. 1084-1089.*

S. Shokouhi et al., "A Noninvasive LSO-APD Blood Radioactivity Monitor for PET Imaging Studies," *IEEE Transactions on Nuclear Science*, vol. 50, No. 5, pp. 1457-1461, Oct. 2003.

M. Itoh et al., "Noninvasive Determination of Arterial Input of $^{15}$O Tracers, Using a Dual Cutaneous β-Detector Set Above the Radial Artery," *Quantification of Brain Function Using PET*, Chapter 14, Academic Press Inc., pp. 67-71, 1996.

(Continued)

*Primary Examiner* — Dennis M White
(74) *Attorney, Agent, or Firm* — Fay Kaplun & Marcin, LLP

(57) ABSTRACT

A blood counting device comprises a capillary conduit for drawing from a subject in which a radiotracer has previously been injected a quantity of blood in the micro-liter range to produce in the capillary conduit a flow of blood from which beta radiation is emitted. At least one direct beta radiation detector is placed closely adjacent to the capillary conduit. The direct beta radiation detector consists of a semiconductor photodiode which detects the beta radiation from the flow of blood when directly hit by this beta radiation.

10 Claims, 5 Drawing Sheets

OTHER PUBLICATIONS

F. Pain et al., "Arterial Input Function Measurement Without Blood Sampling Using a β-Microprobe in Rats," *The Journal of Nuclear Medicine*, vol. 45, No. 9, pp. 1577-1582, Sep. 2004.

N. Kudomi et al., "Development of a GSO Detector Assembly for a Continuous Blood Sampling System," *IEEE Transactions on Nuclear Science*, vol. 50, No. 1, pp. 70-73, Feb. 2003.

L. Eriksson et al., "Automated Blood Sampling Systems for Positron Emission Topography," *IEEE Transactions on Nuclear Science*, vol. 35, No. 1, pp. 703-707, Feb. 1998.

D. Lapoimte et al., "A Microvolumetric Blood Counter/Sampler for Metabolic PET Studies in Small Animals," *IEEE Transactions on Nuclear Science*, vol. 45, No. 4, pp. 2195-2199, Aug. 1998.

A. Villanueva et al., "Spatial Resolution of a Noninvasive Measurement of the Arterial and Venous Input Function Using a Wrist Monitor," *IEEE Nuclear Science Symposium Conference Record* 2003, vol. 4, pp. 2232-2236, Oct. 2003.

A. Kriplani et al., "Noninvasive High-Resolution Detection of Arterial and Venous Input Function Through a PET Wrist Scanner," *IEEE Nuclear Science Symposium Conference Record* 2005, vol. 4, pp. 2240-2244, Oct. 2005.

Kudomi et al., "Development of a GSO Detector Assembly for a Continuous Blood Sampling System," Feb. 2003, IEEE Transactions on Nuclear Science, vol. 50, No. 1, pp. 70-73.

Boellaard et al., "Characteristics of a New Fully Programmable Blood Sampling Device for Monitoring Blood Radioactivity During PET," Jan. 2001, European Journal of Nuclear Medicine, vol. 28, No. 1, pp. 81-89.

\* cited by examiner

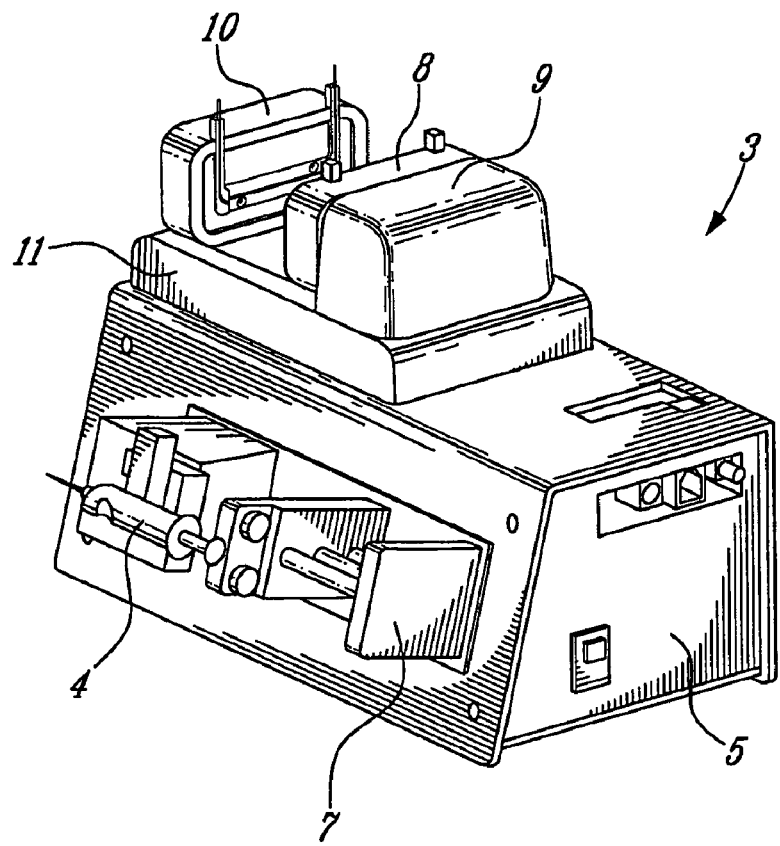
FIG_2
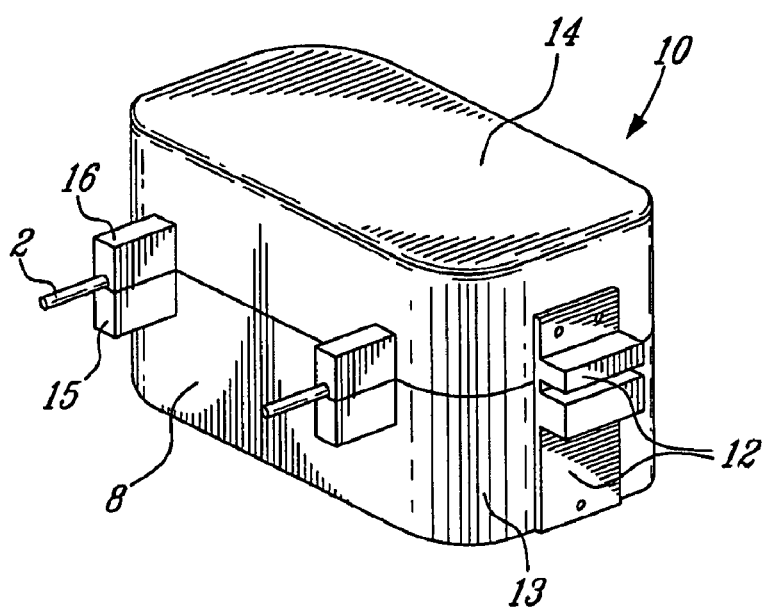
FIG_3

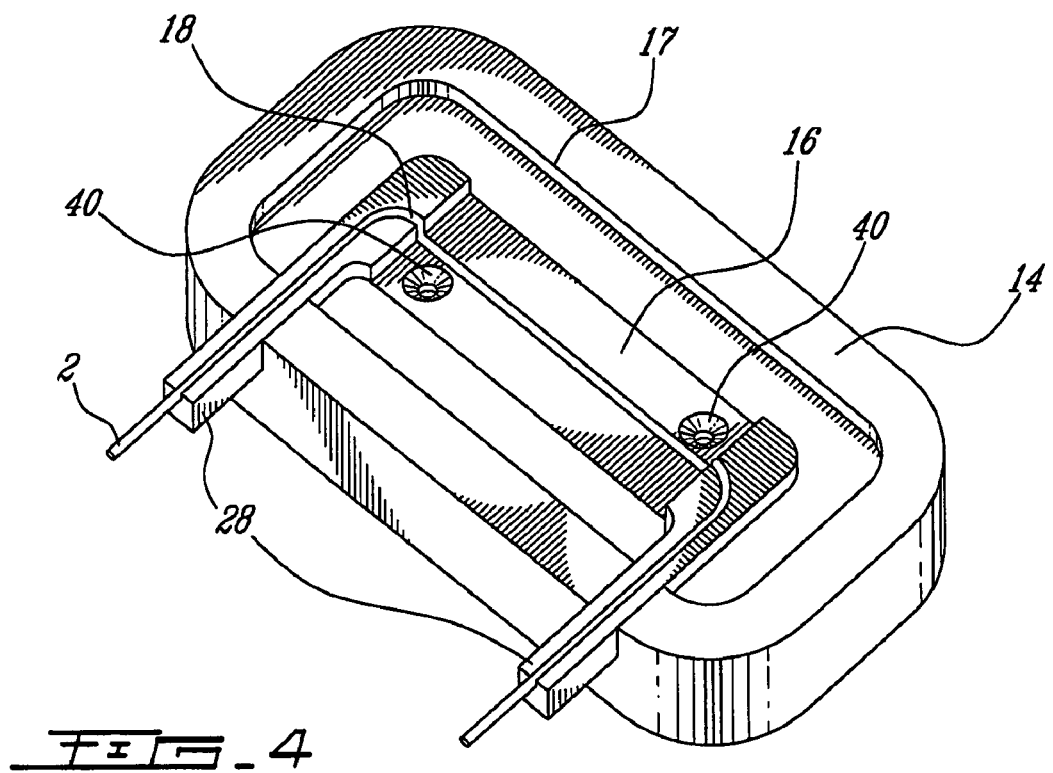
FIG_4
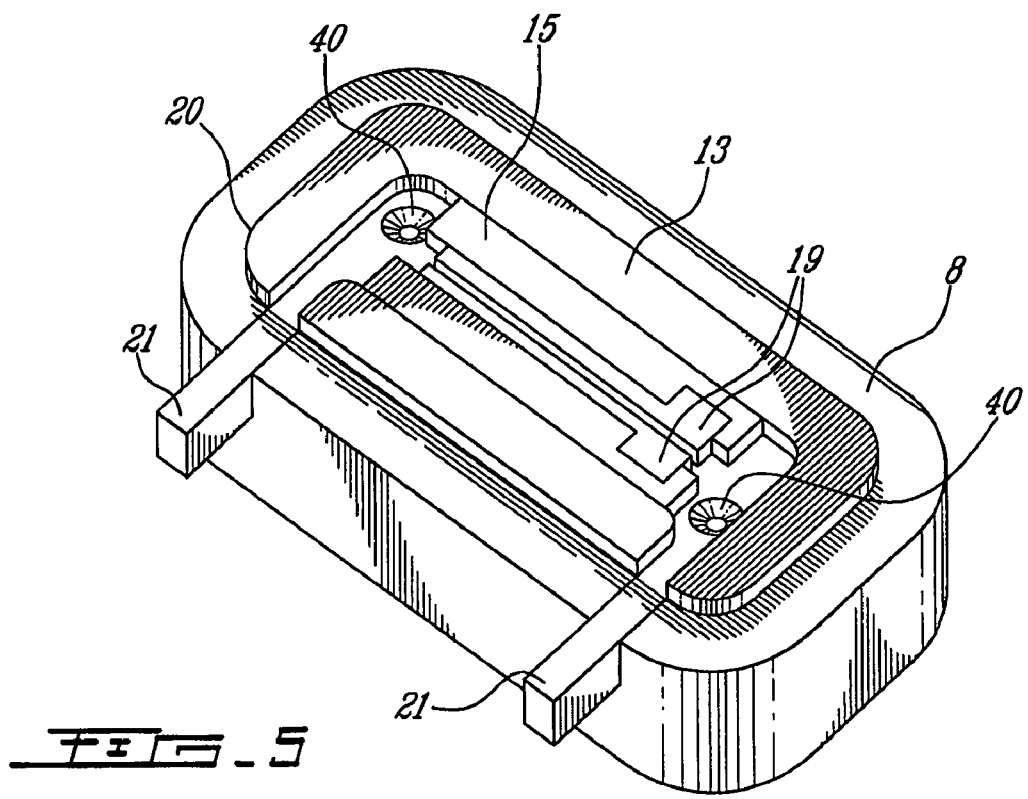
FIG_5

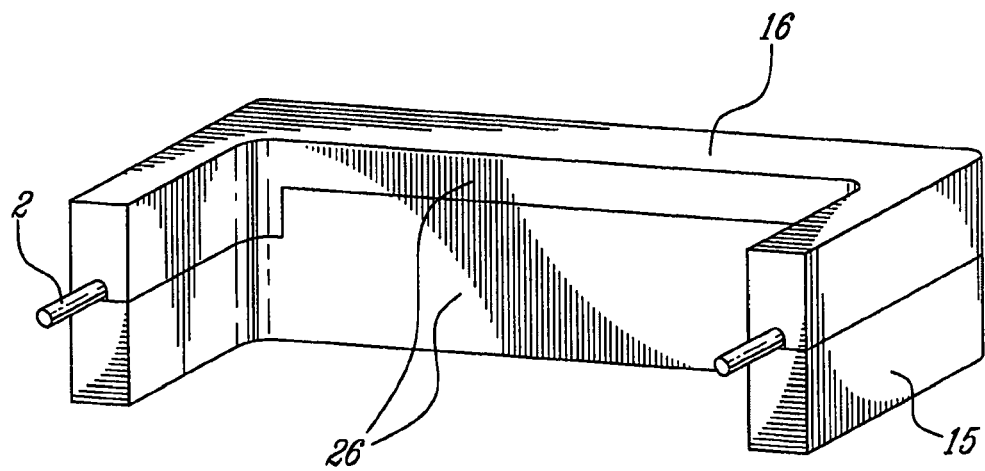
FIG_8
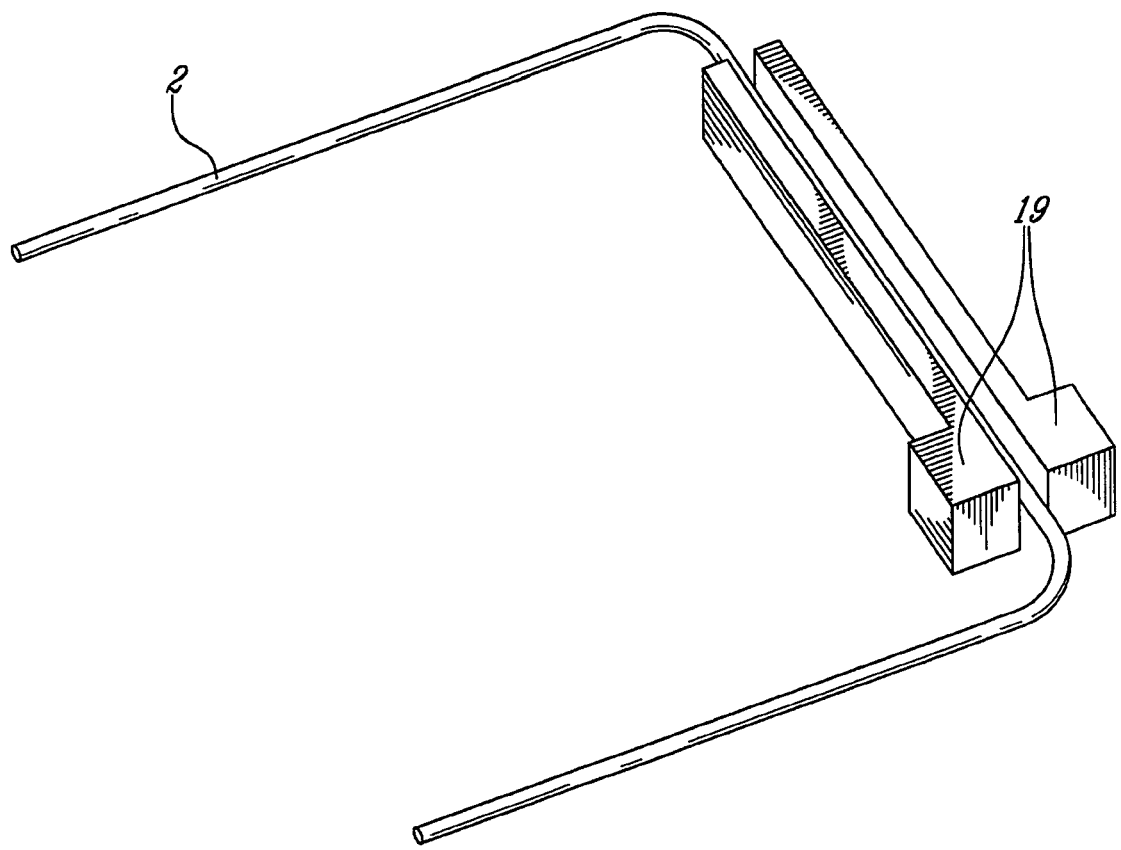
FIG_9

MICRO-VOLUMETRIC BLOOD RADIOACTIVITY COUNTER

PRIORITY CLAIM

This application claims the benefit of U.S. Provisional Patent Application No. 60/662,387 filed on Mar. 17, 2005, the specification of which is expressly incorporated herein, in its entirety, by reference.

FIELD OF THE INVENTION

The present invention relates to a detector assembly, a blood counting method and a blood counting device using the detector assembly. In particular, but not exclusively, the present invention relates to a method and device for measuring in vivo the activity of a radiotracer in the microvolumetric volume of the blood as a function of time and for determining the concentration of the radiotracer in the blood as a function of time in order to establish a kinetic model of the radiotracer.

BACKGOUND OF THE INVENTION

Kinetic modeling of radiotracers in vivo requires determination of the concentration of the radiotracer in blood as a function of time following an intravenous bolus injection of the radiotracer. This usually involves manually taking several arterial blood samples after administration of the radiotracer and counting radioactivity of the samples in a well counter, which requires fairly large amounts of blood. It is also labor-intensive and time consuming. In pre-clinical pharmacokinetic studies performed on small living subjects such as rats and mice, the procedure is further complicated by the small amount of available blood and the difficulty to draw several blood samples in the very short time frame required for kinetic modeling during the first several seconds following bolus injection of the radiotracer.

During pharmacokinetic studies of small living subjects, manual sampling can be replaced by automated blood sampling or non-invasive radioactivity counting techniques. The latter techniques involve an external measurement of the radioactive tracer in arterial blood. With positron emitting radiotracers, this can be done by means of very high resolution mini-positron emission tomography (PET) systems ([Villanueva A. et al., IEEE Trans. Nucl. Sci. (2003)] [Itoh M. et al., Academic Press Inc., Chap. 14, p. 67-71]) placed over a blood vessel. Although these PET systems are suitable for non obese human subjects, they are unsuitable for studying small living subjects because the size of the small living subjects is too small compared to the size of the detector. External measurements can also be obtained using a standard high resolution PET imaging system by selecting a blood cavity as a region of interest, usually the left ventricle of the heart of the small living subject. The latter technique is often used in cardiac PET studies, but positioning the heart of the living subject within the field of view of the scanner is not always possible when imaging other organs. Moreover, time resolution, sensitivity and spatial resolution are often insufficient to obtain accurate blood concentration. Another non-invasive technique involves averaging on a population of interest. Accurate quantification is difficult with this technique due to normal physiological fluctuations between subjects. Furthermore, non-invasive techniques measure whole blood radioactivity concentration so that prior knowledge on plasmatic dispatching of the used radiotracer or some manual samples are required.

Invasive techniques can be divided in systems requiring blood sampling and systems requiring no blood sampling. To avoid loss of living subject blood, it is possible to implant a microprobe directly into the blood vessel [Pain F. et al., J Nucl Med 2004, 45:1577-1582]. Such systems have no dispersion and no catheter absorption but require the insertion of another probe in adjacent tissues for background correction. Furthermore, probe position in artery and artery diameter are uncontrolled parameters that influence sensitivity. Direct quantification is then rather difficult. Many systems with blood sampling have been developed to measure input function. Most of them detect a coincident pair of 511 keV annihilation photons, emitted as a result of the annihilation of the positron with an electron, such as the system described in [Kudomi N. et al., IEEE Trans. Nucl Sci. 2003, Vol. 50, No. 1]. Although coincidence detection mostly suppresses background radiation, heavy shielding is required to shield the detector from the radiation in the living subject. Even though such systems yield a good sensitivity, the size of the detector and shielding is too large to enable positioning the detector very close to the subject and, as a result, a large dead volume is introduced between the subject and the detector. Dealing with small living animals lying in a small animal PET scanner involves using a compact detector and shielding as well as a small dead volume. This type of detector also has to be calibrated frequently. Other invasive devices have been proposed which detect direct positron with plastic scintillator and photomultiplier tube ([Eriksson L. et al., IEEE Trans. Nucl. Sci. 1988, Vol. 35, No. 1] [Lapointe D. et al., IEEE Trans. Nucl. Sci. 1998, Vol. 45, No. 4]. Despite lower detection efficiency than annihilation photon detection, direct beta radiation detectors are less sensitive to background radioactivity. The acquisition electronics is very simple and the overall dimension is more suitable. However there is still a drawback because the scintillator remains somewhat sensitive to gamma radiation from the measured blood sample and from external radiation sources, including the radioactivity within the subject. The latter still makes shielding of the detector rather cumbersome.

SUMMARY OF THE INVENTION

To overcome the above-discussed drawbacks, there is provided, in accordance with the present invention, a blood counting device comprising: a capillary conduit for drawing from a subject in which a radiotracer has previously been injected a quantity of blood in the micro-liter range to produce in the capillary conduit a flow of blood from which beta radiation is emitted; and at least one direct beta radiation detector placed closely adjacent to the capillary conduit, wherein the direct beta radiation detector consists of a semiconductor photodiode which detects the beta radiation from the flow of blood when directly hit by this beta radiation.

The foregoing and other objects, advantages and features of the present invention will become more apparent upon reading of the following non-restrictive description of an illustrative embodiment thereof, given by way of example only with reference to the accompanying drawings.

BRIEF DESCRIPTION OF THE DRAWINGS

In the appended drawings:

FIG. 2 is a perspective view of the blood counting device of the system of FIG. 1;

FIG. 3 is a perspective view of a detector assembly of the blood counting device of FIGS. 1 and 2;

FIG. 4 is a perspective view of a detector cap forming part of the detector assembly of FIG. 3;

FIG. 5 is a perspective view of a detector base forming part of the detector assembly of FIG. 3;

FIG. 8 is a perspective view of a Faraday cup forming part of the detector assembly of FIG. 3; and FIG. 9 is a perspective view showing the position of beta radiation detectors in relation to a catheter.

DETAILED DESCRIPTION

A non-restrictive illustrative embodiment of the blood counting device according to the present invention will now be described. A non-restrictive illustrative embodiment of the blood counting method will be described concurrently.

Figure 1:
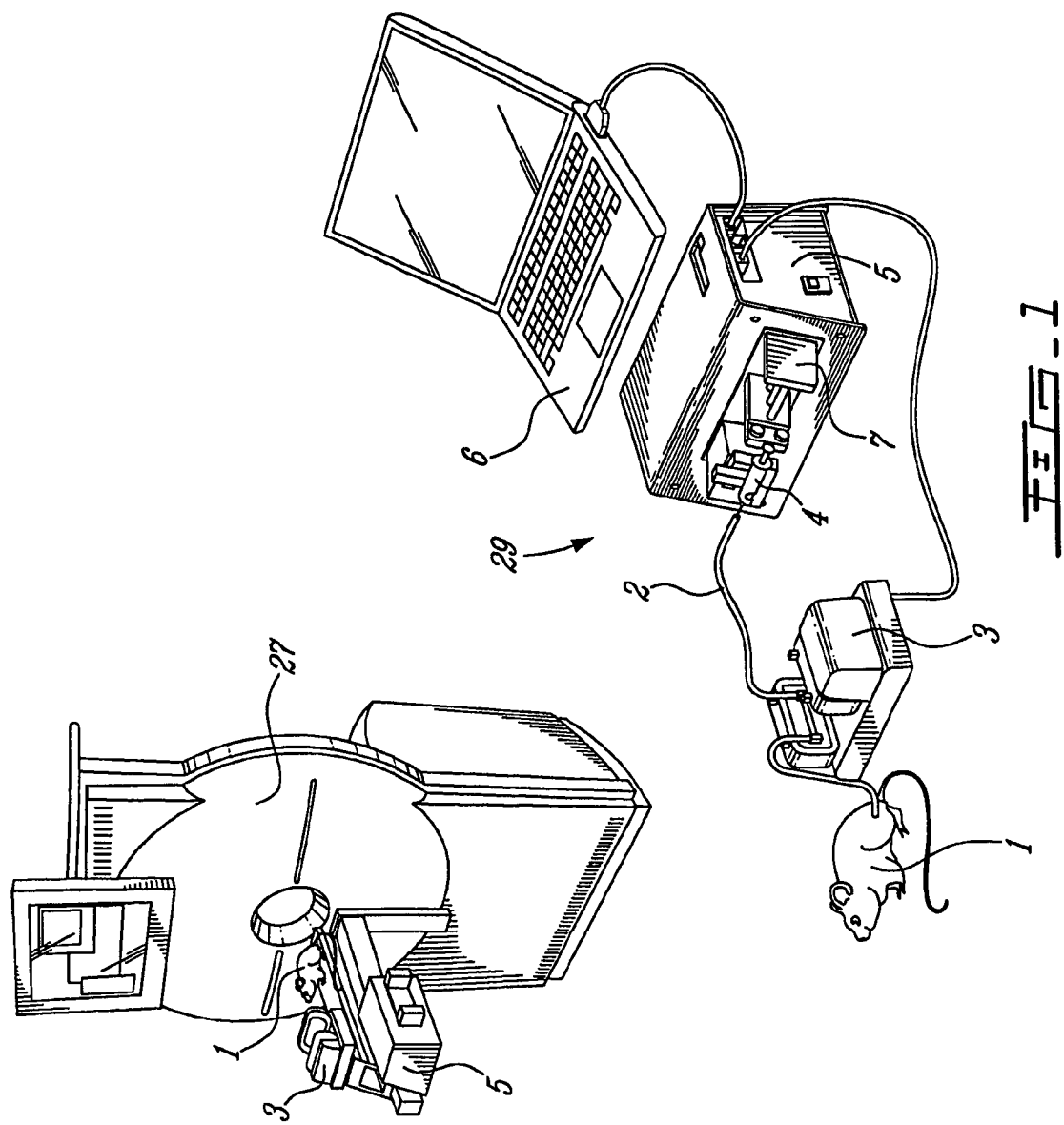
FIG. 1 is a schematic perspective view of a system including a blood counting device according to an illustrative embodiment of the present invention.

Referring to FIG. 1, the blood counting device is generally identified by the reference 29. The blood counting device 29 can be used as a stand-alone apparatus coupled to a personal computer 6 or integrated to a PET scanner 27, as shown in FIG. 1.

The blood counting device 29 comprises a main unit 5, a pumping unit 7 and a detector assembly 3. The main unit 5 incorporates the electronics to control the pumping unit 7 and the detector assembly 3, and to communicate with the personal computer 6 or the PET scanner 27, which are both equipped with software for remote control, data analysis and display. This fully integrated system and software are designed to be user friendly, reduce staff exposure to radiation and increase throughput of pharmacokinetic studies in biomedical and pharmaceutical research.

Blood, for example a micro-volumetric quantity of arterial or venous blood is drawn from a subject 1, for example a living mouse or rat, using a catheter 2, for example PE50 tubing. More specifically, the blood is drawn through the catheter 2 across the detector assembly 3 by the pumping unit 7.

As shown in FIG. 2, the detector assembly 3 comprises a detector cap 10, a detector base 8 and an electronic casing 9 mounted on a rail member 11.

The detector cap 10 holds the catheter 2. Since the cannula (not shown) installed on the subject 1 is often very sensitive to catheter movement, the detector cap 10 is fixed and remains motionless on the rail member 11. Also, the subject 1 is positioned and maintained at the height of the detector assembly 3, close to the detector cap 10 to shorten as much as possible the length of the catheter 2 and, in this way, minimize radioactivity dispersion and time shift between blood counter data and actual blood activity concentration within the subject 1.

The pumping unit 7 comprises a powered, mechanically operated syringe 4 to pump or draw blood from the subject 1. One end of the catheter 2 is mounted on the needle of the syringe 4. Unit 7 is oriented so as to position the syringe 4 with the needle close to the detector cap 10. This configuration, as shown in FIG. 1, contributes to shorten the length of the catheter 2 and maintain the catheter 2 as straight as possible. The syringe pump can be replaced by a peristaltic pump in a closed loop where blood is returned to the animal through a venous catheter.

The detector base 8 holds the beta radiation detectors 19 (FIG. 5) and is attached to the electronic casing 9.

The electronic casing 9 encloses an electronic circuit (not shown) for amplifying, shaping and converting the signals from the beta radiation detectors 19 into digital pulses, setting a level of a detection threshold, and communicating with the main unit 5. These pulses can be counted by the computer 6 or PET scanner 27 to provide a resulting count rate of the blood counting device. To enable placement of the catheter, the detector base 8 can be separated from the detector cap 10 and slid away on the rail member 11 a sufficient distance, for example a distance of up to around 5 cm. Once the catheter 2 is set into place on the detector cap 10, the detector base 8 can then be brought close to the detector cap 10 and the detector assembly 3 closed through bindings such as, for example bindings 12 as shown in FIG. 3. Obviously, any other type of suitable bindings could be used for that purpose.

The rail member 11 contributes to prevent movement of the catheter 2 during closure of the detector assembly 3 and allows only limited movement between the detector cap 10 and the detector base 8. The rail member 11 also makes the detector assembly 3 a full entity that can be fastened on top of the main unit 5, as shown in FIG. 2, or placed aside of that main unit 5 as shown in FIG. 1.

Referring to FIGS. 5 and 9, a pair of beta radiation detectors 19 are mounted on the detector base 8. It should be noted here that the blood counting device could operate with only one beta radiation detector and with more than two beta radiation detectors. The beta radiation detectors 19 are direct beta radiation detectors made of a pair of silicon photodiodes, for example with an active area of 3 mm×30 mm and a 1.5 mm overall thickness. As better shown in FIG. 9, the beta radiation detectors 19 are placed face to face on opposite sides along the catheter 2 through which blood is being drawn to enhance efficiency of detection of beta particles. Silicon photodiodes are very efficient at detecting beta radiation emitted from most typical radioisotopes used as radiotracers in clinical and biological studies, such as $^{11}C$, $^{13}N$, $^{15}F$, $^{64}Cu$, $^{131}I$, etc., and rather insensitive to the X, gamma or annihilation radiation emitted by these radioisotopes. As a result, silicon photodiodes will not be affected in a significant manner by gamma rays emitted from the small amount of radioactivity contained in the blood within the catheter. Moreover, due to the insensitivity of photodiodes to high energy gamma rays, as well as the small size and compact arrangement of photodiodes around the catheter, the resulting detector assembly 3 can be protected from external radiation sources, including the relatively high radioactivity within the subject, with a very thin shielding.

The distance between the silicon photodiodes and the blood within the catheter 2 is kept as short as possible as the range of detection of beta particles is short. With common PE50 tubing, the detection volume within the catheter 2 between the pair of photodiodes is 8 μl and the blood radioactivity concentration scale is in kBq/μl or nCi/μl.

As indicated in the foregoing description, the beta radiation detectors 19 detects very small blood radioactivity level inside the catheter 2 from beta radiation without contamination by the very large amount of radioactivity, in the several MBq or mCi range, which is present within the subject 1. Therefore, silicon PIN photodiodes having a fairly thick depleted region at the junction are selected since they are highly sensitive to beta radiation while remaining rather insensitive to X, gamma and annihilation radiation. Radiation shielding needed to protect the silicon photodiodes against external gamma radiation can then be very compact.

Blood inside the catheter forms an efficient conducting medium acting like an antenna for external EMI (electromagnetic interference) and, therefore, brings EMI very close to the very sensitive silicon photodiodes, often producing an interference signal of non-negligible amplitude. Some EMI shielding is thus provided.

Finally, silicon photodiodes are very sensitive to ambient light and must be operated in the dark. Mechanical and electrical filtering can be used to avoid such disruptions.

Referring to FIGS. 3, 4 and 5, the enclosure of the detector assembly 3 is made of two complementary external layers 13 and 14. The detector assembly 3 also comprises internal linings 15 and 16 both having grooves with appropriate curvatures to accommodate the catheter 2 in order to provide a light-tight assembly for the beta radiation detectors 19. The internal linings 15 and 16 can be screwed to the inner faces of the external layer 13 and 14, respective, through beveled holes such as 40. The external layers 13 and 14 shield the beta radiation detectors 19 against external X, gamma or annihilation radiation, whereas the internal linings 15 and 16 shield the beta radiation detectors 19 against external EMI.

The external layers 13 and 14 of the detector assembly enclosure are made of dense and heavy material, such as lead, tungsten or similar high atomic number materials, with a sufficient thickness to substantially absorb external X, gamma or annihilation radiation and prevent such external radiation to reach the beta radiation detectors 19. As shown in FIGS. 4 and 5, the detector cap 10 comprises a shallow cavity 17 and the detector base 8 comprises a complementary embossment 20 whereby the detector base 8 and cap 10 of the detector assembly 3 interlock to protect the beta radiation detectors 19 from external X, gamma or annihilation radiation. The complementary cavity 17 and embossment 20 also contribute to protect the beta radiation detectors 19 from external light.

The catheter 2 could lead a small amount of light to the beta radiation detectors 19; it is kept negligible by the curves such as 18 and extensions 21 and 28, for example approximately 10 mm long, of the internal linings 15 and 16, respectively. The extensions 21 and 28 also contribute to reduce EMI sensitivity.

The internal linings 15 and 16 are U-shaped and made of copper or another anti-EMI material to enclose the beta radiation detectors 19 and the catheter 2. As illustrated in FIG. 8, the internal linings 15 and 16 form a Faraday cup 26 that provides effective shielding against EMI from the surrounding equipment(s).

The internal linings 15 and 16 also provide an easy and reproducible catheter 2 "vs" beta radiation detectors 19 relative positioning, therefore leading to a reproducible calibration of the device.

Figure 6:
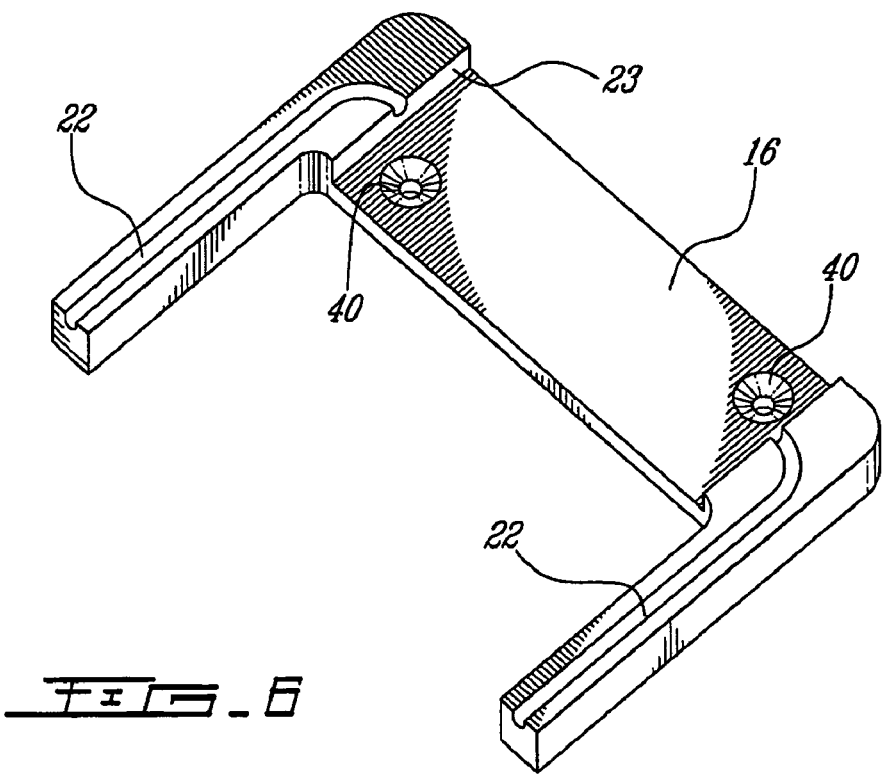
FIG. 6 is a perspective view of an internal lining of the detector cap of FIG. 4.

More specifically, as shown in FIG. 6, the legs of the U-shaped internal lining 16 of the detector cap 10 defines groove sections 22 having a size suitable to easily receive and secure the catheter 2 in place. The base of the U-shaped internal lining 16 defines a generally rectangular cavity 23.

Figure 7:
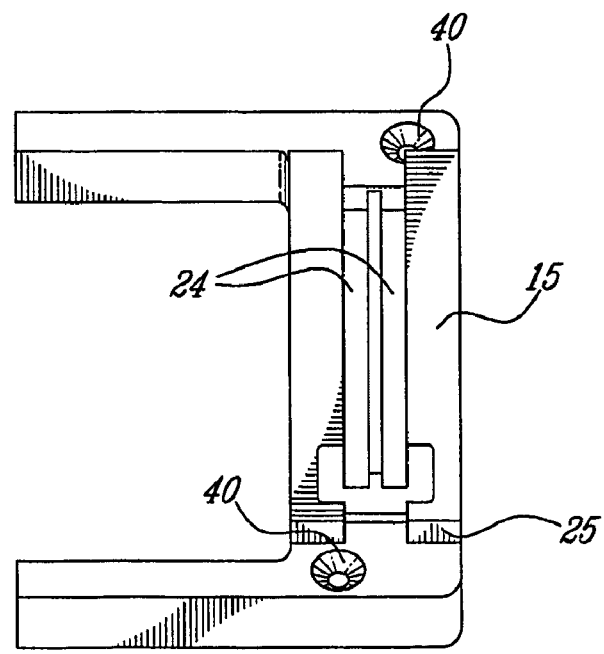
FIG. 7 is a perspective view of an internal lining of the detector base of FIG. 5.

Referring now to FIG. 7, the internal lining 15 of the detector base 8 defines, in an embossment 25 complementary to the cavity 23, two grooves 24 to receive and position the beta radiation detectors 19 in such a manner that they face each other with a proper spacing therebetween to insert the catheter 2 with no dead space between the catheter and the confronting faces of the detectors 19.

The cavity 23, embossment 25 and internal linings 15 and 16 form a tight interlocking assembly forming the Faraday Cup 26 and that position accurately the catheter 2 between the respective active areas of the beta radiation detectors 19 as shown in FIG. 9.

Measured absolute sensitivity and sensitivity limits for a PE50-type catheter (PE50 tubing) and four common radioisotopes are reported in the following Table 1. Efficiency losses are minimized by the use of thin wall PE catheter and optimal geometry.

TABLE 1

|  | $E_{\beta max}$ (Mev) | Emission Probability | Other Particles | Sensitivity limit | Absolute Sensitivity |
|---|---|---|---|---|---|
| $^{18}$F | 0.634 | 96.7% | γ (511 keV) | 11.5 kBq/µl | 7% |
| $^{64}$Cu | 0.578, 0.653 | 55.1% | γ (511, 1346 keV) | 24 kBq/µl | 3% |
| $^{13}$N | 1.199 | 99.8% | γ (511 keV) | 3.7 kBq/µl | 23% |
| $^{11}$C | 0.96 | 99.7% | γ (511 keV) | 5.5 kBq/µl | 16% |

More specifically, with PE50 capillary tubing, a typical sensitivity of 10 to 30 cps/(kBq/µl) [0.4 to 1 cps/(nCi/µl)] is obtained for the most popular PET radioisotopes ($^{18}$F, $^{13}$N, $^{11}$C, $^{64}$Cu). Due to its mechanical design and compact shielding, the sensitivity of the blood counting device to radioactive background is only 5 cps for a 37 MBq (1 mCi) $^{18}$F source 10 cm away from the detectors 19.

The small size of the beta radiation detectors 19 and shielding enables the design of a small-dimension detector assembly 3 that can be placed on the bed, having for example a size of 8 cm×30 cm, of a typical small subject PET scanner 27 as shown in FIG. 1. The main unit 5 can be coupled to the bed of the PET scanner 27 whereby the subject 1, the catheter 2, the detector assembly 3, the main unit 5 and the pumping unit 7 move with the bed of the PET scanner 27 as the subject 1 is placed in the camera field of view.

The blood counting method and device according to the non-restrictive illustrative embodiment can be used, in particular but not exclusively to measure a blood time-activity curve in real time as micro-volumetric amounts of blood are drawn from the subject 1, for example a living subject 1 through the catheter 2. The subject 1 can be a small laboratory animal, such as a mouse, a rat, a hamster, a rabbit, etc. The blood counting method and device is also suitable for use with humans. The blood counting device may be qualified as a flow-through blood counting device.

The blood counting device may include, amongst others the following features and/or advantages:

direct beta (positron or electron) detection is performed using semiconductor photodiodes;

the size of the blood counting device, and particularly of the detector assembly, is kept to a minimum contrary to prior technologies using, for example, scintillation crystals coupled to a photomultiplier tube;

due to the geometry of the blood counting device, detection efficiency is maximized and catheter placement is highly reproducible, thus absolute calibration is stable and reproducible;

as the device draws blood from a subject, it can be easily coupled to an automated sampling device to collect microvolumes of blood as a time-activity curve is being measured so that further analysis can be performed to determine plasma and metabolites activity as a function of time and final correction can be applied to the time-activity curve;

direct detection of beta particles with a semiconductor photodiode minimizes the detector size next to the subject and reduces the sensitivity of the blood counting device to ambient gamma radiation;

when using small catheter tubing, such as PE50 (0.58 mm ID, 0.965 mm OD), a large fraction of the beta particles emitted from the radiotracers in the blood have sufficient energy to cross the catheter wall and escape from the tube;

the radiation detectors are highly sensitive to beta particles (electrons or positrons) but rather insensitive to gamma radiation, annihilation radiation (511 keV) or X-rays emitted from the radioactive nuclides present in the blood;

the radiation detectors are arranged in pair in a compact configuration surrounding almost completely the catheter containing blood over a sufficient length to achieve high detection efficiency for beta particles;

an electronic acquisition circuit can be provided consisting of a charge sensitive preamplifier, a shaping amplifier and a microcontroller used to set a discriminator level and register event counts in real time;

the blood pumping unit can be programmable to draw small amounts of arterial or venous blood into a small catheter (e.g., PE50 tubing) at a suitable rate for measuring the time-activity curve in pharmacokinetic studies of radiotracers;

hardware and software can be provided for automatically adjusting a lower level discriminator in such a manner as to reduce the background noise count rate to a pre-selected value;

a programmable controller can be set-up to automatically control the blood pumping unit, blood counting device and the electronic hardware to display the detector count rate in real time and record data in local memory or transfer them to a computer;

dedicated software can be provided to process recorded data and display a blood time-activity curve in real time, as it is being measured, including required corrections such as radioisotope decay, absolute sensitivity calibration, detector dead time, time lag and radioactivity dispersion; and hardware and software can be provided to incorporate the blood counting data into a list mode data stream of an imaging device such as, for example a positron emission tomography (PET) scanner.

Although the present invention has been described in the foregoing description by way of a non-restrictive illustrative embodiment, this embodiment can be modified at will within the scope of the appended claims without departing from the spirit and nature of the subject invention.

What is claimed is:

1. A blood counting device comprising:
a shielding enclosure defining therein a U-shaped channel for receiving a capillary conduit adapted to draw from a subject in which a radiotracer has previously been injected a quantity of blood in the micro-liter range to produce in the capillary conduit a flow of blood from which beta radiation is emitted, the U-shaped channel comprising first and second opposite end sections, the generally straight section of the capillary conduit being placed between the first and second sections; and
at least one elongated direct beta radiation detector placed within the enclosure, extending along the generally straight section of the capillary conduit and closely adjacent to the generally straight section of the capillary conduit, wherein the at least one detector consists of a semiconductor photodiode which detects the beta radiation from the flow of blood when directly hit by the beta radiation.

2. A blood counting device as defined in claim 1, wherein the at least one detector includes a pair of elongated direct beta radiation detectors extending along the generally straight section of the capillary conduit on opposite sides of the U-shaped channel.

3. A blood counting device as defined in claim 2, wherein the U-shaped channel is structured to position, in a reproducible manner, the capillary conduit between the detectors thereby achieving reproducible detection efficiency calibration.

4. A blood counting device as defined in claim 1, wherein the shielding enclosure comprises a shielding structure for shielding the semiconductor photodiode against at least one of the following radiations: light, X-ray, gamma radiation, annihilation radiation, and electromagnetic interference.

5. A blood counting device according to claim 1, further comprising a processor of the detected beta radiation configured to measure a level of activity of the radiotracer as a function of time and to display the measured level of activity in predetermined units of radioactivity and in real time during the measurement.

6. A blood counting device as defined in claim 1, wherein the subject is a small animal selected from the group consisting of a mouse, a rat, a hamster, and a rabbit, and wherein the total quantity of blood drawn from the subject is a small fraction of the total subject blood volume to prevent affecting physiological conditions of the subject.

7. A blood counting device as defined in claim 1, wherein, while the semiconductor photodiode is sensitive to beta radiation, the semiconductor photodiode is substantially insensitive to gamma radiation.

8. A blood counting device as defined in claim 1, wherein the blood counting device using the semiconductor photodiode as direct beta radiation detector has dimensions that fit on a bed of a small animal PET scanner.

9. A blood counting device comprising:
a capillary conduit for drawing from a subject in which a radiotracer has previously been injected a quantity of blood in the micro-liter range to produce in the capillary conduit a flow of blood from which beta radiation is emitted;
at least one elongated direct beta radiation detector extending along and closely adjacent to a generally straight section of the capillary conduit; and
a shielding enclosure defining therein a U-shaped channel for receiving the capillary conduit, the U-shaped channel comprising first and second opposite end sections, the generally straight section of the capillary conduit being placed between the first and second sections,
wherein the at least one detector consists of a semiconductor photodiode which detects the beta radiation from the flow of blood when directly hit by the beta radiation.

10. A blood counting device as defined in claim 9, wherein the at least one detector includes a pair of elongated direct beta radiation detectors extending along the generally straight section of the capillary conduit on opposite sides of the U-shaped channel.

* * * * *